United States Patent
Buelow et al.

(10) Patent No.: US 9,678,644 B2
(45) Date of Patent: Jun. 13, 2017

(54) DISPLAYING A PLURALITY OF REGISTERED IMAGES

(75) Inventors: Thomas Buelow, Grosshansdorf (DE); Martin Bergtholdt, Hamburg (DE); Kirsten Regina Meetz, Hamburg (DE); Ingwer-Curt Carlsen, Hamburg (DE); Rafael Wiemker, Kisdorf (DE)

(73) Assignee: Koninklijke Philips N.V., Eindhoven (NL)

( * ) Notice: Subject to any disclaimer, the term of this patent is extended or adjusted under 35 U.S.C. 154(b) by 562 days.

(21) Appl. No.: 14/128,668

(22) PCT Filed: Jun. 27, 2012

(86) PCT No.: PCT/IB2012/053259
§ 371 (c)(1),
(2), (4) Date: Feb. 20, 2014

(87) PCT Pub. No.: WO2013/001471
PCT Pub. Date: Jan. 3, 2013

(65) Prior Publication Data
US 2015/0363080 A1    Dec. 17, 2015

(30) Foreign Application Priority Data
Jun. 29, 2011   (EP) .................................... 11171859

(51) Int. Cl.
*G06F 3/0484*   (2013.01)
*G06T 19/20*   (2011.01)
(Continued)

(52) U.S. Cl.
CPC ........ *G06F 3/04845* (2013.01); *G06F 3/0482* (2013.01); *G06F 3/0488* (2013.01);
(Continued)

(58) Field of Classification Search
CPC ... G06F 3/00; G06F 3/01; G06F 3/048; G06F 3/0481; G06F 3/0482; G06F 3/0484;
(Continued)

(56) References Cited

U.S. PATENT DOCUMENTS

| 5,613,013 A * | 3/1997 | Schuette | G06K 9/32 356/400 |
|---|---|---|---|
| 7,693,349 B2 | 4/2010 | Gering | |

(Continued)

FOREIGN PATENT DOCUMENTS

CN    1846616 A    10/2006

OTHER PUBLICATIONS

Buelow, T. et al "Segmentation of Suspicious Lesions in Dynamic Contrast-Enhanced Breast MR Images", SPIE Medical Imaging, CAD, vol. 6514, No. 27, 2007.
(Continued)

*Primary Examiner* — Xiomar L Bautista (57) ABSTRACT

A system for displaying a plurality of registered images is disclosed. A first viewport unit displays a representation of a first image dataset in a first viewport. A second viewport unit displays a representation of a second image dataset in a second viewport. A position indication unit enables a user to indicate a position in the first dataset displayed in the first viewport, to obtain a user-indicated position. A corresponding position determining unit determines a position in the second image dataset corresponding to the user-indicated position, to obtain a corresponding position in the second image dataset, based on correspondence information mapping positions in the first image dataset to corresponding positions in the second image dataset. The second viewport unit displays an indication of the corresponding position in the second viewport.

16 Claims, 3 Drawing Sheets

| 200 | display unit |
|---|---|
| 201 | first viewport |
| 202 | second viewport |
| 203 | second viewport |
| 204 | second viewport |
| 205 | second viewport |
| 206 | second viewport |
| 207 | object |
| 207' | outline |
| 208 | object |
| 209 | object |
| 210 | object |
| 211 | object |
| 212 | object |

(51) Int. Cl.
*G06F 3/0482* (2013.01)
*G06F 3/0488* (2013.01)
*G06F 19/00* (2011.01)

(52) U.S. Cl.
CPC ........ *G06F 3/04842* (2013.01); *G06F 19/321* (2013.01); *G06T 19/20* (2013.01); *G06T 2219/028* (2013.01); *G06T 2219/2004* (2013.01)

(58) Field of Classification Search
CPC ......... G06F 9/4443; G06T 7/00; G06T 11/00; G06T 11/60; G06T 19/20; G06K 9/32; A61N 5/00; A61B 5/05
See application file for complete search history.

(56) References Cited

U.S. PATENT DOCUMENTS

| 7,708,682 | B2* | 5/2010 | Pekar | A61N 5/103 382/131 |
|---|---|---|---|---|
| 2008/0267483 | A1* | 10/2008 | Zhan | G06K 9/32 382/131 |
| 2010/0021082 | A1 | 1/2010 | Declerck | |
| 2010/0317967 | A1 | 12/2010 | Carlsen | |
| 2011/0200227 | A1* | 8/2011 | Bogoni | G06F 19/321 382/103 |
| 2011/0268336 | A1 | 11/2011 | Dmitrieva et al. | |
| 2012/0123801 | A1* | 5/2012 | Opfer | A61B 6/037 705/3 |
| 2012/0134562 | A1* | 5/2012 | Boettger | A61B 6/5235 382/131 |

OTHER PUBLICATIONS

Meyer, C.R. et al "Quantitative Imaging to Assess Tumor Response to Therapy: Common Themes of Measurement, Truth, Data, and Error Sources", Translational Oncology, vol. 2, No. 4, Dec. 2009, pp. 198-210.

Opfer, Roland et al "Automatic Lesion tracking for a PET/CT based Computer Aided Cancer Therapy Monitoring System", Medical Imaging 2008, Computer-Aided Diagnosis, Proc. of SPIE, vol. 6915.

Kanakatte, Aparna et al "Pulmonary Tumor Volume Delineation in PET Images using Deformable Models", 30th Annual International IEEE EMBS Conference, 2008.

Song, Soo-Min et al "Coregistration of Small Animal PET and Autoradiongraphy for in Vivo-Ex Vivo Comparison", Progress in Pattern Recognition, Image Analysis and Applications. 2007, pp. 822-830.

Brock, K.K. et al "Feasibility of a Novel Deformable Image Registration Technique to Facilitate Classification, Targeting, and Monitoring of Tumor and Normal Tissue", International Journal of Radiation: Oncology Biology Physics, vol. 64, No. 4, Mar. 2006.

* cited by examiner

FIG. 1

| 200 | display unit |
| 201 | first viewport |
| 202 | second viewport |
| 203 | second viewport |
| 204 | second viewport |
| 205 | second viewport |
| 206 | second viewport |
| 207 | object |
| 207' | outline |
| 208 | object |
| 209 | object |
| 210 | object |
| 211 | object |
| 212 | object |

FIG. 2

| 301 | displaying a representation of a first image dataset |
|---|---|
| 302 | displaying a representation of a second image dataset |
| 303 | enabling a user to indicate a position in the first dataset displayed in the first viewport |
| 304 | determining a position in the second image dataset corresponding to the user-indicated position |
| 305 | displaying an indication of the corresponding position in the second viewport |

FIG. 3

DISPLAYING A PLURALITY OF REGISTERED IMAGES

CROSS-REFERENCE TO PRIOR APPLICATIONS

This application is the U.S. National Phase application under 35 U.S.C. §371 of International Application No. PCT/IB2012/053259, filed on Jun. 27, 2012, which claims the benefit of European patent application Ser. No.11171859.9, filed on Jun. 29, 2011. These applications are hereby incorporated by reference herein.

FIELD OF THE INVENTION

The invention relates to displaying a plurality of registered images.

BACKGROUND OF THE INVENTION

The success of chemotherapeutic treatment of cancer is not the same for each patient, cancer type, or treatment type. In the case that the treatment does not have an optimal result, it may be possible to take action to improve the situation, for example by adapting the treatment regimen. To this effect, the therapy response of a tumor can be monitored during the therapy. Medical imaging, e.g. magnetic resonance (MR) imaging, provides data from which the therapy response of a tumor can be deduced. For example, MR scans may be taken before treatment and after at least part of the treatment has been performed. This way, the tumor may be tracked over time and the response to the treatment can be assessed. For example, the size of a tumor may be measured using a medical workstation. However, currently used manual measurements are of limited robustness and reproducibility. Tracking a tumor over time requires it to be found and labeled in the image data, which is a time-consuming process.

The paper "Quantitative imaging to assess tumor response to therapy: common themes of measurement, truth data, and error sources" by C. R. Meyer et al., Translational Oncology, Vol. 2, No. 4, December 2009, pp. 198-210, discloses multiple, image modality-independent means to assess the relative performance of algorithms for measuring tumor change in response to therapy.

U.S. Pat. No. 7,708,682 B2 discloses a method and an apparatus for planning radiation therapy. A radiation dose distribution is adapted on the basis of shape and position variations of the organs of interest, determined from a comparison of a first image and a second image taken at different points in time during the radiation treatment process. A surface mesh is first adapted to the surface of the object of interest in the first image and then to the surface of interest in the second image. Then, a difference between the two adapted surface meshes is determined.

SUMMARY OF THE INVENTION

It would be advantageous to have an improved display of a plurality of registered images. To better address this concern, a first aspect of the invention provides a system comprising a first viewport for displaying a representation of a first image dataset;

a second viewport for displaying a representation of a second image dataset;

a position indication unit for enabling a user to indicate a position in the first dataset displayed in the first viewport, to obtain a user-indicated position; and a corresponding position determining unit for determining a position in the second image dataset corresponding to the user-indicated position, to obtain a corresponding position in the second image dataset, based on correspondence information mapping positions in the first image to corresponding positions in the second image;

wherein the second viewport is arranged for displaying an indication of the corresponding position in the second viewport.

This system allows easier and faster comparison of the first image and the second image, since the user only needs to indicate a structure of interest, e.g., a tumor in the first image, and the corresponding structure is automatically indicated in the second viewport. By means of a single click, automatic quantification of the tumor in both images can be triggered. It is not necessary to deform or warp the display of either the first or the second image, as is frequently done in existing systems to display elastic registration results, so that the user can understand which positions of the images correspond to each other. Instead, for any user-indicated position, the corresponding position in the other image is displayed. This is important, because in the setting of therapy response assessment the user identifies changes of the tumor of interest. If warping is applied, these changes would be mixed up with the artificial deformations.

The first image may represent an object and may be associated with a first acquisition time, and the second image may represent the same object and may be associated with a different acquisition time. The correspondence information may represent a deformation of the object between the acquisition times. This kind of image data and correspondence information represents an important application of the described techniques. By indicating a position in the first viewport, the user may simultaneously indicate the position in the second viewport, because this indication is provided automatically, based on the correspondence information. Since both images relate to the same object, it is possible to initiate for example processing steps, based on the positions in both images, at the same time.

The second viewport may be arranged for displaying an outline of at least part of the object associated with the first acquisition time, based on the first image and/or the correspondence information. This facilitates the comparison of the shape of the object at the first and second acquisition times.

The second viewport may be arranged for displaying a slice of the second image. The system may further comprise a slice selector for selecting a slice comprising the corresponding position. This is particularly interesting when at least one of the image datasets represents three-dimensional (or higher-dimensional) images. A slice view may be generated to display a slice of the three- or higher dimensional image. However, the user-indicated position and the corresponding position are not necessarily in the same slice, making it difficult to view corresponding structures in both viewports. Therefore, the second viewport may be arranged to adjust the displayed slice according to the corresponding position.

The correspondence information may comprise rigid registration information to account for a rotation or a translation of at least part of the object represented by the images and non-rigid registration information to account for a deformation of the object, wherein the second viewport is arranged for rotating or translating the second image, based on the rigid registration information, and wherein the display of the indication of the corresponding position is based on the non-rigid registration information. This is an advantageous combination of adjusting the display of the object in the second viewport (based only on rotation/translation) and providing the indication of the corresponding position to enable further comparison between the images. The rotation/translation facilitates the comparison of the object between the two viewports, without removing any differences in shape. The system may furthermore allow accurately visually comparing the first image with the second image by locally applying a rigid transformation, e.g., a rotation of the structure of interest in the second viewport, so that anatomically corresponding cross-sections of the structure of interest are displayed and a meaningful comparison is possible.

The correspondence information may comprise a first shape model that is adapted to the first image dataset and a second shape model that is adapted to the second image dataset. This is an effective way to generate the correspondence information. Alternatively or additionally, the correspondence information can e.g. be derived by a rigid or elastic registration algorithm.

The position indication unit may be arranged for enabling the user to indicate the user-indicated position by positioning a mouse cursor on the first viewport. This allows easy indication of the user-indicated position.

The position indication unit may be arranged for enabling the user to indicate the user-indicated position by means of a touch screen. This allows easy indication of the user-indicated position.

The position indication unit may be arranged for enabling the user to input a sequence of successive user-indicated positions by moving a pointer over the first viewport, wherein the correspondence determining unit is arranged for updating the corresponding position as the pointer is moved over the first viewport, and the second viewport is arranged for updating the display of the indication of the corresponding position as the corresponding position is updated. This provides a particularly pleasing effect, making it easy to view a large number of corresponding positions in a short time.

The system may comprise a plurality of second viewports, for enabling display of a plurality of respective second image datasets having correspondence information associated therewith. The correspondence determining unit may be arranged for determining the respective corresponding positions in the plurality of second images, based on the indicated position and the correspondence information. The plurality of second viewports may be arranged for displaying respective indications of the respective corresponding positions in the respective viewports. This way, a position in a structure may be indicated in any number of images, by indicating the position in only one of the images.

The first image dataset and the respective second image datasets may be part of a time sequence of acquired images of an object. This allows viewing the indication of the corresponding positions in a time sequence of images of an object.

The system may comprise a manual correction unit for enabling a user to correct at least part of the correspondence information by indicating a landmark position in at least one of the images. This allows the user to override any automatically generated correspondence information.

In another aspect, the invention provides a workstation comprising a system set forth. In yet another aspect, the invention provides an image acquisition apparatus comprising a scanner to obtain one or more or all of the image datasets, and a system set forth for displaying a plurality of registered images.

In another aspect, the invention provides a method of displaying a plurality of registered images, comprising
 displaying a representation of a first image dataset;
 displaying a representation of a second image dataset;
 enabling a user to indicate a position in the first dataset displayed in the first viewport, to obtain a user-indicated position;
 determining a position in the second image dataset corresponding to the user-indicated position, to obtain a corresponding position in the second image dataset, based on correspondence information mapping positions in the first image to corresponding positions in the second image; and
 displaying an indication of the corresponding position in the second viewport.

In another aspect, the invention provides a computer program product comprising instructions for causing a processor system to perform a method set forth herein.

It will be appreciated by those skilled in the art that two or more of the above-mentioned embodiments, implementations, and/or aspects of the invention may be combined in any way deemed useful. It will be understood that the techniques described herein apply to two-dimensional, three-dimensional, four-dimensional, and higher-dimensional image datasets. These image datasets may be acquired by means of any suitable image acquisition apparatus, such as a digital camera, an x-ray apparatus, a computed tomography apparatus, a magnetic resonance apparatus, a nuclear medicine-based scanner, or an ultrasound apparatus.

Modifications and variations of the image acquisition apparatus, the workstation, the system, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from the above and will be elucidated hereinafter with reference to the drawings, in which.

DETAILED DESCRIPTION OF EMBODIMENTS

Figure 1:
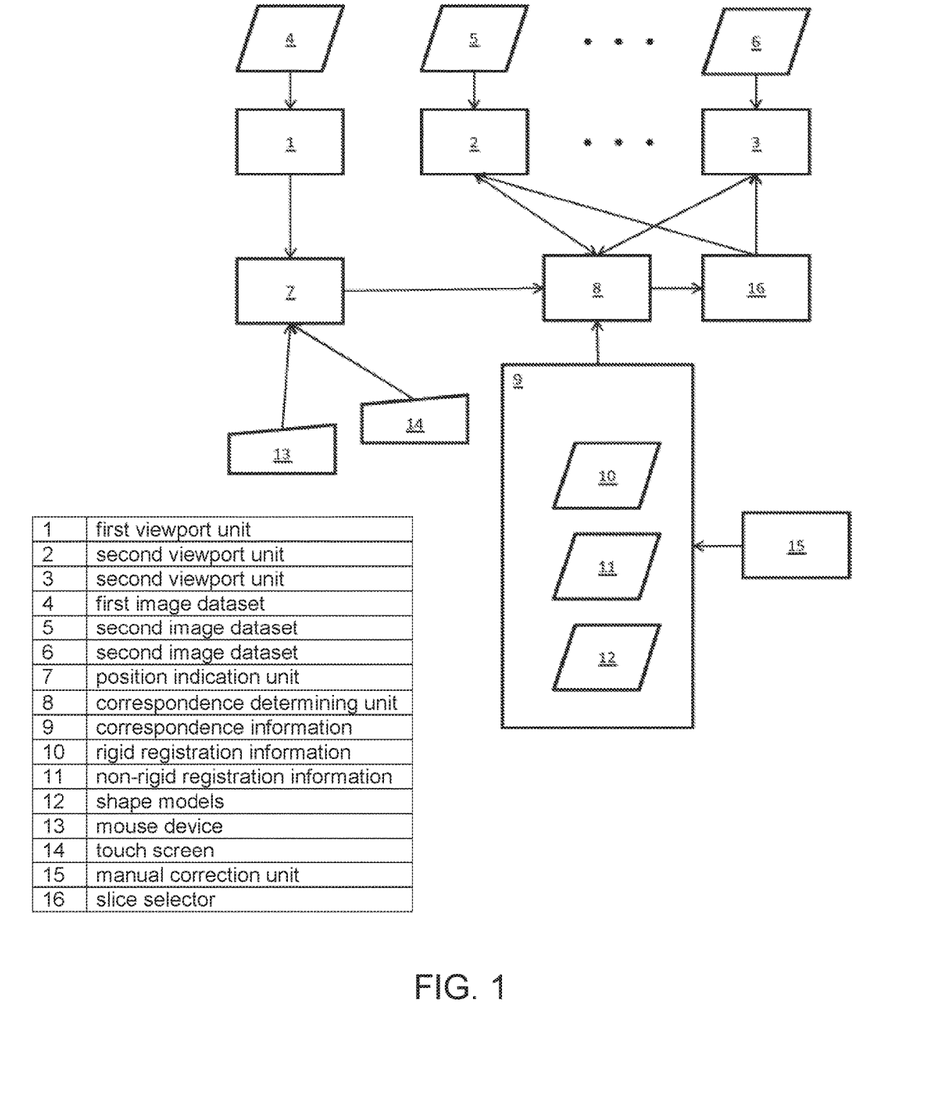
FIG. 1 is a block diagram of a system for displaying a plurality of registered images.

FIG. 1 illustrates an example of a system for displaying a plurality of registered images. It is noted that many of the elements shown in the drawing are optional or may be replaced by an equivalent item. The system may be implemented, for example, on a computer system by means of a suitable computer program. The computer system may consist of a workstation. The computer system may also be part of a distributed computer system that may have many functionalities, such as storage and distribution of images and/or other information. An example of such a distributed system is a picture archiving and communications system (PACS). The system may comprise a display unit for displaying the images and other information, and a user input device such as a mouse and keyboard. The display and the user input device may be integrated into a touch screen.

Figure 2:
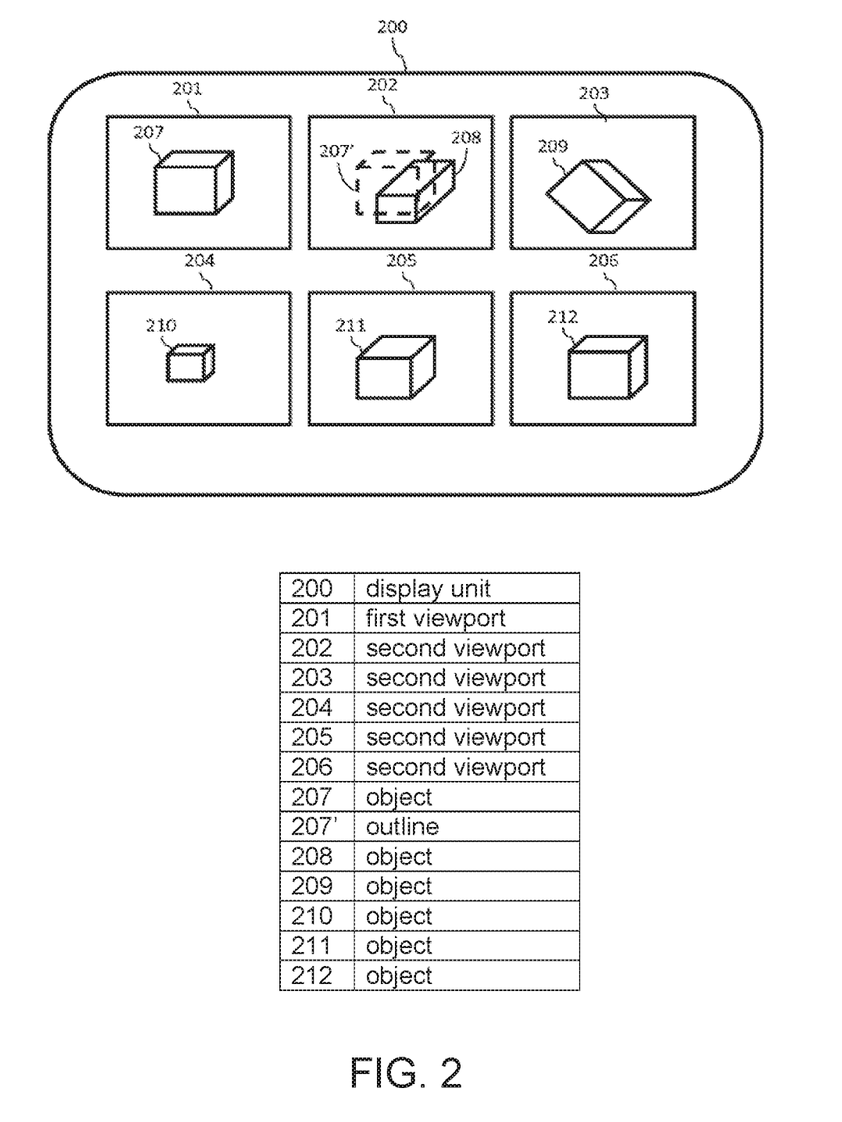
FIG. 2 is a sketch of a screenshot produced by the system or method described herein.

FIG. 2 illustrates a display unit 200 showing a plurality of viewports 201-206. The number of six viewports in the drawing is only an arbitrary example. Any number of two or more viewports can be used. A viewport should be understood to be an area of the display in which a particular item is displayed. In the following description, the system will be explained with reference to both FIGS. 1 and 2.

The system may comprise a first viewport unit 1 for controlling the first viewport 201. The system may comprise a second viewport unit 2 for controlling the second viewport 202. Similarly, the system may comprise a plurality of second viewport units 2, 3 arranged for controlling a plurality of second viewports 202-206. As an example, the second viewport units 2, 3 may be implemented using the same, or copies of the same, software code, with differing parameters such as different image datasets and different viewport coordinates to operate on.

The first viewport unit 1 may be arranged for displaying a representation of a first image dataset 4 in the first viewport 201. For example, a maximum intensity projection, a surface rendering, or a slice view may be displayed in the case of an at least three-dimensional image dataset. In the case of a two-dimensional image dataset, the image dataset may be visualized in a way known in the art per se. The second viewport unit 2 may be arranged for displaying a representation of a second image dataset 5 in the second viewport 202. The second viewport unit may be using the same rendering technique as, or a different rendering technique than, the first viewport unit.

The system may comprise a position indication unit 7 arranged for enabling a user to indicate a position in the first dataset 4 displayed in the first viewport 201. The indication may be performed in a way known in the art per se, to obtain a user-indicated position in the first image dataset. For example, in the case of a slice view, the position in a three-dimensional space can be derived from the position indicated in the viewport and the parameters of the slice, such as the slice number.

The system may comprise a corresponding position determining unit 8 arranged for determining a position in the second image dataset 5 corresponding to the user-indicated position. This way, a corresponding position in the second image dataset 5 is obtained. To this end, correspondence information 9 mapping positions in the first image dataset 4 to corresponding positions in the second image dataset 5 is used. The correspondence information 9 may be interpolated, if necessary, to find the corresponding position for the user-indicated position.

The second viewport unit 2 may be arranged for displaying an indication of the corresponding position in the second viewport 202. For example, an arrow may be shown that points to the corresponding position in the second image dataset 5 as shown in the second viewport 202. Alternatively, a dot or another symbol may be displayed. Alternatively, the position may be highlighted by using an alternate color.

The first image dataset 4 may represent an object 207. For example, the first image dataset may be a photograph of the object 207 or may be a medical image of a patient comprising the object 207 as an organ. The first image dataset 4 may be associated with a first acquisition time. Similarly, the second image dataset 5 may represent the same object, wherein the second image dataset 5 may be associated with a different acquisition time. For example, the second image dataset 5 may be obtained using the same imaging modality as the first image dataset 4, or a different imaging modality. The correspondence information 9 may represent a deformation of the object 207 between the acquisition times. FIG. 2 illustrates how the object 207-212 represented in the datasets is shown with different shapes in the respective different viewports 201-206. As an illustrative example, a cubic shape has been used. In practice, the object 207-212 may be an organ or a tumor that changes shape, due to e.g. treatment.

The second viewport unit 2 may be arranged for displaying an outline 207' in the second viewport. This outline 207' is the outline of at least part of the object 207 associated with the first acquisition time, based on the first image. Consequently, it can be observed from the second viewport 202 how the object has changed.

As described above, the second viewport unit 2 may be arranged for displaying a slice of the second image dataset. The system may comprise a slice selector 16 for selecting a slice comprising the corresponding position. The second viewport unit 2 may be arranged to display the selected slice. The second viewport unit 2 may optionally be arranged to include a further graphical indication of the corresponding position.

The correspondence information 9 may comprise rigid registration information 10 to account for a rotation or a translation of at least part of the object represented by the image datasets. Moreover, the correspondence information may comprise non-rigid registration information 11 to account for a deformation of the object, including a change of the size. The second viewport unit 2 may be arranged for rotating or translating the second image dataset, based on the rigid registration information 10. This way, the object is shown as similarly as possible on the first and second viewports, without obscuring any deformation of the object. To allow easy indication of anatomically corresponding points in the plurality of viewports, the display of the indication of the corresponding position is based on the non-rigid registration information 11.

The correspondence information 9 may comprise one or more shape models 12. A first shape model may be adapted to the first image dataset 4 and a second shape model may be adapted to the second image dataset 5. The corresponding positions may be coded by means of these shape models, in a way known in the art per se.

The position indication unit 7 may be arranged for enabling the user to indicate the user-indicated position by positioning a mouse cursor on the first viewport. To this end, the position indication unit may be operatively connected to a mouse device 13 or a trackball or touchpad or other pointing means. Alternatively, the user may be enabled to touch a touch screen 14 showing the first viewport at the desired position.

The position indication unit 7 may be arranged for enabling the user to input a sequence of successive user-indicated positions by moving a pointer over the first viewport. The correspondence determining unit 8 may be arranged for updating the corresponding position as the pointer is moved over the first viewport. The second viewport unit 2 may be arranged for updating the display of the indication of the corresponding position as the corresponding position is updated. This way, a real-time response may be implemented. Moreover, the display may be fluently updated as the user hovers the pointer over the first viewport.

As described above, a plurality of second viewport units 2, 3 may be supported. This enables display of a plurality of respective second image datasets 5, 6 having correspondence information 9 associated therewith. The correspondence determining unit 8 may be arranged for determining the corresponding positions in each one of the plurality of second image datasets 5, 6, based on the indicated position and the correspondence information 9. The plurality of second viewport units 2, 3 may be arranged for displaying respective indications of the respective corresponding positions in the respective second viewports 202-206. These positions may also be fluently updated, as described above.

The first image dataset 4 and the respective second image datasets 5, 6 may be part of a time sequence of acquired images of an object.

The system may comprise a manual correction unit 15 for enabling a user to correct at least part of the correspondence information by indicating a landmark position in at least one of the images, in a way known in the art per se.

The system may be incorporated in the image viewing portion of an image acquisition apparatus. Such an apparatus may comprise the image scanner (such as a CT scanner or x-ray apparatus) that is used for acquiring the first image dataset and/or the second image dataset.

Figure 3:
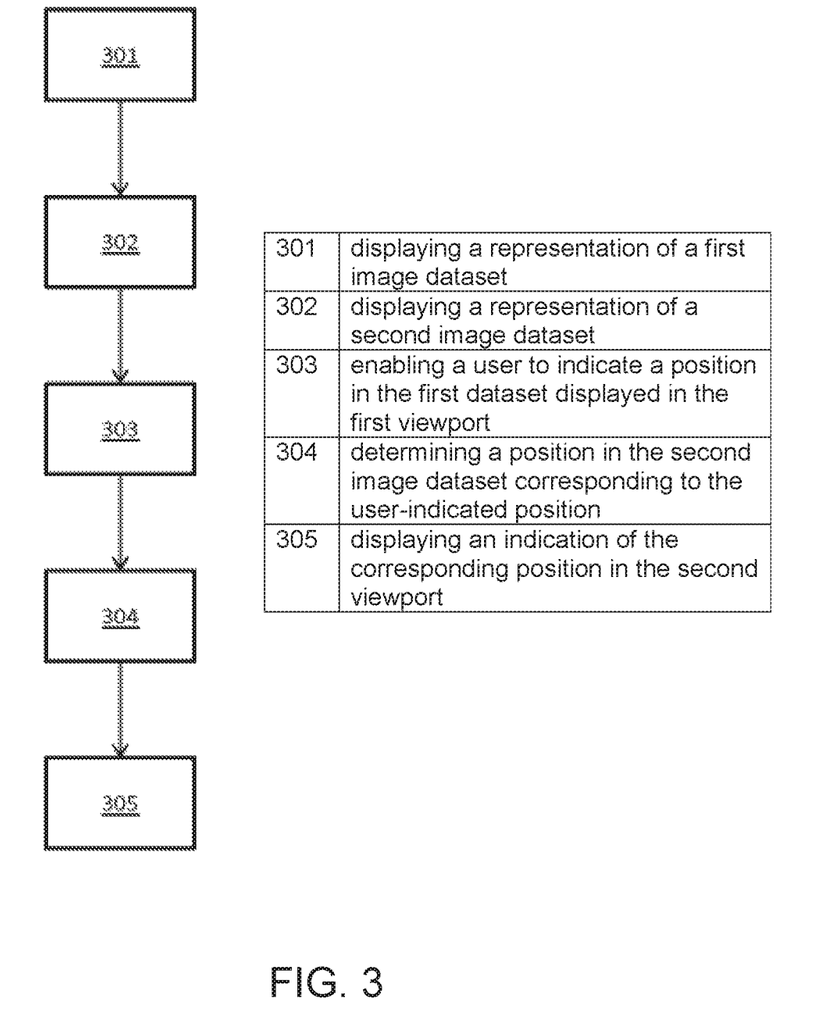
FIG. 3 is a flowchart showing steps of a method of displaying a plurality of registered images.

FIG. 3 illustrates a method of displaying a plurality of registered images. The method comprises a step 301 of displaying a representation of a first image dataset. The method may further comprise a step 302 of displaying a representation of a second image dataset. The method may further comprise a step 303 of enabling a user to indicate a position in the first dataset displayed in the first viewport, to obtain a user-indicated position. The method may further comprise a step 304 of determining a position in the second image dataset corresponding to the user-indicated position, to obtain a corresponding position in the second image dataset, based on correspondence information mapping positions in the first image to corresponding positions in the second image. The method may further comprise a step 305 of displaying an indication of the corresponding position in the second viewport. The method may be adapted by the skilled person in view of this description. The method may be implemented by means of a computer program.

The success of chemotherapeutic treatment of cancer is not the same for each patient, cancer type, or treatment type. In order to react in case of an unsuccessful treatment (e.g., by adapting the treatment regimen), it is useful to monitor the therapy response of a tumor during the therapy. Medical imaging, e.g. MR imaging, provides data from which the therapy response of a tumor can be deduced. Currently used manual measurements are of limited robustness and reproducibility. For tracking a tumor over time it has to be found and labeled in the image data, which is a time-consuming process.

A graphical user interface may be provided comprising a plurality of viewports as described above, allowing inspecting one baseline and a series of follow-up images side-by-side. An algorithm for automatic identification of anatomically corresponding positions in base-line and follow-up images (e.g. an elastic registration algorithm) and a UI that updates corresponding mouse pointer positions in real time may be provided. An underlying database may be used to store corresponding image information along with information about the geometric deformation between the image content of corresponding images. An interaction scheme for manual adjustment of the misplaced lesion locations may be provided. Algorithms for quantitative feature extraction from the tumor images may be provided.

When the system is in operation, new image data may be imported into a PACS-like database and screened for pairs of image volumes that can be meaningfully linked to each other, e.g. two image volumes from two different MR examinations of the same patient, which both belong to a dynamic contrast-enhanced series and were taken at about the same time point in the dynamic acquisition. Depending on the available algorithms for geometric linkage of image data, other pairs of image volumes may also be included as corresponding volumes.

A user interface may allow the user to access the database and select an examination as base-line examination, identify an image volume from this examination as base-line volume, and offers corresponding volumes from later examinations (according to the database information) as possible follow up images volumes.

After loading the selected image volumes, the images are shown in separate viewports, e.g. as shown in FIG. 2. The user can then select a tumor in the baseline image. The anatomically corresponding positions may be shown in the follow-up images and updated in realtime as the user indicates a different position. The correspondence information can, e.g., be derived by application of an elastic registration algorithm to a base-line/follow-up image pair. The user can mark the tumor in one image and the tumor positions may be propagated to the other images, using the registration information, and subsequently stored in the image database. Using the tumor location, automatic tumor segmentation may be applied and the change in tumor value over time may be plotted to show a trend of the tumor reaction to the treatment. Such automatic tumor segmentation is known from, for example, Buelow, T., Meinel, L. A., Wiemker, R., Kose, U., Shimauchi, A., and Newstead, G., "Segmentation of suspicious lesions in dynamic contrast-enhanced breast MR images," in SPIE Medical Imaging: CAD, 6514, 27 (2007).

The tumor may be marked in all corresponding examinations. An automatic segmentation algorithm may be applied to delineate the tumor. The computed tumor volumes may be graphically shown. Given the tumor location (and tumor segmentation), other features can be computed, such as kinetic features, based on dynamic contrast-enhanced imaging studies, apparent diffusion coefficients derived from diffusion-weighted images or morphologic features. Optionally, the deformation vector field derived by the elastic registration can be used in order to align the tumor subvolumes (which might be tilted and rotated due to variations in patient positioning). This allows the user to visually compare corresponding cross sections of the tumor. Tumor subvolumes may be aligned with the orientation of the tumor in the baseline image in order to obtain corresponding tumor cross section images. The tumor delineation may be computed from the base line image and superimposed on the corresponding position of the follow up images. Optionally, the tumor contour as derived by the segmentation of the tumor in the baseline image volume can be shown graphically in the corresponding position of the follow up images in order to allow visual comparison of tumor change over time.

The system can be used in any radiology workstation, PACS system or on a scanner console.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be subdivided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via an electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or to be used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for displaying a plurality of registered images, comprising
a first viewport unit for displaying a representation of a first image dataset in a first viewport;
a second viewport unit for displaying a representation of a second image dataset in a second viewport; wherein the second image dataset is obtained using the same imaging modality as the first image dataset;
a position indication unit for enabling a user to indicate a position in the first image dataset displayed in the first viewport, to obtain a user-indicated position; and
a corresponding position determining unit for determining a position in the second image dataset corresponding to the user-indicated position, to obtain a corresponding position in the second image dataset, based on correspondence information mapping positions in the first image dataset to corresponding positions in the second image dataset;
wherein the second viewport unit is arranged for displaying an indication of the corresponding position in the second viewport.

2. The system according to claim 1, wherein the first image dataset represents an object and is associated with a first acquisition time, and the second image dataset represents the same object and is associated with a different acquisition time, and wherein the correspondence information represents a deformation of the object between the acquisition times.

3. The system according to claim 2, wherein the second viewport unit is arranged for displaying an outline of at least part of the object associated with the first acquisition time, based on the first image and/or the correspondence information.

4. The system according to claim 2, wherein the correspondence information comprises rigid registration information to account for a rotation or a translation of at least part of the object represented by the image datasets and non-rigid registration information to account for a deformation of the object, wherein the second viewport unit is arranged for rotating or translating the second image dataset, based on the rigid registration information, and wherein the display of the indication of the corresponding position is based on the non-rigid registration information.

5. The system according to claim 1, wherein the second viewport unit is arranged for displaying a slice of the second image dataset, and comprises a slice selector for selecting a slice comprising the corresponding position.

6. The system according to claim 1, wherein the correspondence information comprises a first shape model that is adapted to the first image dataset and a second shape model that is adapted to the second image dataset.

7. The system according to claim 1, wherein the position indication unit is arranged for enabling the user to indicate the user-indicated position by positioning a mouse cursor on the first viewport or touching the position on a touch screen showing the first viewport.

8. The system according to claim 1, wherein the position indication unit is arranged for enabling the user to input a sequence of successive user-indicated positions by moving a pointer over the first viewport, and wherein the correspondence determining unit is arranged for updating the corresponding position as the pointer is moved over the first viewport, and the second viewport unit is arranged for updating the display of the indication of the corresponding position as the corresponding position is updated.

9. The system according to claim 1, comprising a plurality of second viewport units arranged for controlling a plurality of second viewports, for enabling display of a plurality of respective second image datasets having correspondence information associated therewith, wherein the correspondence determining unit is arranged for determining the corresponding positions in the plurality of second image datasets, based on the indicated position and the correspondence information, and wherein the plurality of second viewport units are arranged for displaying respective indications of the respective corresponding positions in the respective second viewports.

10. The system according to claim 9, wherein the first image dataset and the respective second image datasets are part of a time sequence of acquired images of an object.

11. The system according to claim 1, wherein the system comprises a manual correction unit for enabling a user to correct at least part of the correspondence information by indicating a landmark position in at least one of the images.

12. A workstation comprising a system according to claim 1.

13. An image acquisition apparatus comprising an image scanner for acquiring the first image dataset and/or the second image dataset, and a system according to claim 1.

14. A method of displaying a plurality of registered images, comprising
- displaying a representation of a first image dataset;
- displaying a representation of a second image dataset, wherein the second image dataset is obtained using the same imaging modality as the first image dataset;
- enabling a user to indicate a position in the first image dataset displayed in the first viewport, to obtain a user-indicated position;
- determining a position in the second image dataset corresponding to the user-indicated position, to obtain a corresponding position in the second image dataset, based on correspondence information mapping positions in the first image dataset to corresponding positions in the second image dataset; and
- displaying an indication of the corresponding position in the second viewport.

15. A non-transitory computer readable storage medium comprising instructions for causing a processor system to perform the method according to claim 14.

16. A system for displaying a plurality of registered images, comprising:
- a display unit configured to display a first viewport and a second viewport;
- a first viewport unit for displaying a representation of a first image dataset in the first viewport;
- a second viewport unit for displaying a representation of a second image dataset in the second viewport; wherein the second image dataset is obtained using the same imaging modality as the first image dataset;
- a position indication unit for enabling a user to indicate a position in the first image dataset displayed in the first viewport, to obtain a user-indicated position; and
- a corresponding position determining unit for determining a position in the second image dataset corresponding to the user-indicated position, to obtain a corresponding position in the second image dataset, based on correspondence information mapping positions in the first image dataset to corresponding positions in the second image dataset;
- wherein the second viewport unit is arranged for displaying an indication of the corresponding position in the second viewport.

* * * * *